(12) United States Patent
Buckland et al.

(10) Patent No.: US 10,940,502 B2
(45) Date of Patent: Mar. 9, 2021

(54) LINEAR DROPLET GENERATING DEVICE

(71) Applicant: TTP Plc, Royston (GB)

(72) Inventors: Justin Buckland, Royston (GB); David Pooley, Royston (GB)

(73) Assignee: TTP Plc, Royston (GB)

( * ) Notice: Subject to any disclaimer, the term of this patent is extended or adjusted under 35 U.S.C. 154(b) by 46 days.

(21) Appl. No.: 15/768,377

(22) PCT Filed: Oct. 6, 2016

(86) PCT No.: PCT/GB2016/053105
§ 371 (c)(1),
(2) Date: Apr. 13, 2018

(87) PCT Pub. No.: WO2017/064473
PCT Pub. Date: Apr. 20, 2017

(65) Prior Publication Data
US 2018/0297053 A1    Oct. 18, 2018

(30) Foreign Application Priority Data

Oct. 16, 2015 (GB) .................................. 1518337

(51) Int. Cl.
*B05B 17/06* (2006.01)
*B05B 7/06* (2006.01)
(Continued)

(52) U.S. Cl.
CPC ...... *B05B 17/0676* (2013.01); *B05B 17/0607* (2013.01); *B05B 17/0638* (2013.01);
(Continued)

(58) Field of Classification Search
CPC ............ B05B 17/0676; B05B 17/0607; B05B 17/0638; B05B 17/0646; B05B 17/0661;
(Continued)

(56) References Cited

U.S. PATENT DOCUMENTS 4,465,234 A * 8/1984 Maehara ............... F23D 11/345
239/102.2
5,444,471 A * 8/1995 Usui ..................... B41J 2/14274
347/72
(Continued)

FOREIGN PATENT DOCUMENTS

EP    0 943 436 A2    9/1999
EP    1 243 417 A2    9/2002
(Continued)

OTHER PUBLICATIONS

International Search Report dated Mar. 9, 2017, in International Application No. PCT/GB2016/053105; Filed: Oct. 6, 2016 Applicant: The Technology Partnership PLC.
(Continued)

*Primary Examiner* — Joseph A Greenlund
(74) *Attorney, Agent, or Firm* — Erise IP, P.A.

(57) ABSTRACT

A nozzle plate (201) for use in a liquid droplet production apparatus and such apparatus, the nozzle plate comprising a flexible substrate having a linear array of nozzles that extend through said plate, said nozzles being arranged in at least one line, forming thereby a nozzle-bearing region, wherein the substrate is curved so as to impart an increased longitudinal stiffness to it. The apparatus comprises a piezo actuator (202, 203), which may have slots (211) separating fingers acting on the nozzle plate (201). The nozzle plate may be separable form the actuator.

25 Claims, 5 Drawing Sheets

(51) Int. Cl.
*B05B 17/00* (2006.01)
*A61M 11/00* (2006.01)
*B06B 1/06* (2006.01)
*G10K 11/36* (2006.01)

(52) U.S. Cl.
CPC ...... *B05B 17/0646* (2013.01); *B05B 17/0661* (2013.01); *B05B 17/0669* (2013.01); *B06B 1/06* (2013.01); *A61M 11/005* (2013.01); *B06B 2201/77* (2013.01); *G10K 11/36* (2013.01)

(58) Field of Classification Search
CPC .............. B05B 17/0669; A61M 11/005; B06B 2201/77
USPC ............................................ 239/102.1, 102.2
See application file for complete search history.

(56) References Cited

U.S. PATENT DOCUMENTS

| | | | | |
|---|---|---|---|---|
| 5,746,373 | A * | 5/1998 | Sanada | B05B 17/0646 239/102.2 |
| 5,960,224 | A * | 9/1999 | Sanada | B05B 17/0646 396/575 |
| 6,394,363 | B1 * | 5/2002 | Arnott | B41J 2/14201 239/102.1 |
| 7,108,197 | B2 * | 9/2006 | Ivri | A61M 11/005 239/102.2 |
| 7,960,894 | B2 * | 6/2011 | Duru | B05B 17/0646 310/317 |
| 2006/0207591 | A1 * | 9/2006 | Gallem | A61M 11/005 128/200.14 |
| 2009/0167812 | A1 * | 7/2009 | Asai | B41J 2/1639 347/20 |
| 2009/0242663 | A1 * | 10/2009 | Yu | A61M 11/005 239/102.2 |
| 2010/0039480 | A1 | 2/2010 | Brown et al. | |
| 2011/0121095 | A1 * | 5/2011 | Crichton | B05B 17/0638 239/102.2 |
| 2011/0168804 | A1 * | 7/2011 | Crichton | B05B 17/0638 239/102.2 |
| 2011/0315786 | A1 | 12/2011 | Kambayashi | |
| 2012/0143152 | A1 * | 6/2012 | Hunter | A61B 5/4839 604/298 |
| 2013/0119151 | A1 * | 5/2013 | Moran | A61M 15/0085 239/102.2 |
| 2013/0150812 | A1 * | 6/2013 | Hunter | B05B 17/0661 604/295 |
| 2014/0110500 | A1 * | 4/2014 | Crichton | B05B 17/0646 239/102.2 |
| 2014/0361095 | A1 * | 12/2014 | Haran | B05B 17/0646 239/4 |
| 2014/0367486 | A1 * | 12/2014 | Kawano | A61L 9/14 239/102.2 |
| 2015/0122906 | A1 * | 5/2015 | Kawano | A01N 25/06 239/1 |
| 2016/0236470 | A1 * | 8/2016 | Mizukami | B41J 2/1629 |
| 2018/0221906 | A1 * | 8/2018 | Anzenberger | B23K 26/3584 |
| 2018/0297053 | A1 * | 10/2018 | Buckland | B05B 17/0661 |

FOREIGN PATENT DOCUMENTS

| | | |
|---|---|---|
| JP | H06 7720 A | 1/1994 |
| WO | 2008/029216 A1 | 3/2008 |
| WO | 2013/090468 A1 | 6/2013 |

OTHER PUBLICATIONS

Written Opinion of the International Searching Authority dated Mar. 9, 2017, in International Application No. PCT/GB2016/053105; Filed: Oct. 6, 2016 Applicant: The Technology Partnership PLC.

* cited by examiner

Figure 1: (below)

LINEAR DROPLET GENERATING DEVICE

RELATED APPLICATIONS

The present application is a national stage application under 35 U.S.C. § 371 of International Application No. PCT/GB2016/053105, filed 6 Oct. 2016, which claims priority to Great Britain Patent Application No. 1518337.9, filed 16 Oct. 2015. The above referenced applications are hereby incorporated by reference into the present application in their entirety.

FIELD OF INVENTION

This invention relates to linear, electrically switchable spray generator for simultaneously generating multiple streams of droplets, and methods of operating such an electrically switchable spray generator.

BACKGROUND TO THE INVENTION

Electronic droplet generators that use ultrasonic vibration to generate liquid droplets are well known in the art and have found use in a wide range of fields including medical drug delivery and the treatment of air (for example fragrance delivery and humidification). A subset of such devices in widespread use (commonly referred to as 'pond misters') use a vibrating surface covered by liquid to cause droplets to be generated through the break-up of standing waves on the liquid free surface (U.S. Pat. No. 3,812,854 being an example). This break-up leads to droplets with a wide range of sizes being produced and shaping of the liquid container above the level of the liquid is used to limit the size range of droplets that escape and are delivered. With a wide range of droplets being contained and returned to the bulk liquid, such devices have low efficiency resulting in high power consumption. The efficiency of such devices can be improved by constraining the free surface of the liquid with a perforate plate or membrane (U.S. Pat. No. 4,533,082 for example). This plate may have just a single nozzle (for dispensing or printing applications for example in which individual drops may be dispensed on demand) or may have many thousands of nozzles (for nebuliser applications for example). Relatively monodisperse droplets are produced when such perforate plates are used in which the droplet diameter is related to the size of the openings, or nozzles, in the perforate plate. Such devices still suffer multiple disadvantages: In particular, the vibrating surface needs to be mounted close to the plate, but not touching, for effective droplet generation and not all liquid in the container can be delivered (as the liquid is required to transmit the pressure waves to the perforate plate). A preferred embodiment of such devices is therefore one in which the perforate plate itself is vibrated by the driver element (commonly called the actuator) with examples including U.S. Pat. No. 4,533,082 and EP 0431992. This enables the delivery of relatively well monodispersed droplets without requiring the pressure waves to be transmitted through a liquid layer, thereby further increasing efficiency and enabling a wider range of embodiments. A preferred embodiment of such a device such as described in U.S. Pat. No. 5,518,179 uses a bending mode actuator to deliver the vibrational energy to the plate as this enables the use of thin low cost actuators and further increases efficiency. A linear format bending mode actuator is described in WO 00/33972. This linear format actuator is able to produce only a limited velocity amplitude and hence a limited amplitude of pressure oscillation in the fluid to drive jetting/droplet ejection. It is also only able to produce a limited degree of uniformity of motion along its length. These factors translate into limitations in the ability to control the droplet size and droplet velocity and limitations in the ability of the device to eject viscous fluids. In addition to this, the device is unable to operate with a nozzle plate which can be separated from the actuator. This is because, in the prior art designs, the nozzle plate must be very firmly attached to the actuator in order to vibrate with high enough amplitude to cause droplet ejection. In practice, this requires a permanent bonding method, for example adhesive bonding. A separable nozzle plate allows removal and replacement of the nozzle plate. This is advantageous as the nozzles can become blocked or damaged during usage. It also allows the user to avoid cross-contamination between different fluids, and enables use of a consumable fluid cartridge, integral with the nozzle plate.

It is the objective of this invention to overcoming the shortcomings in the prior art linear droplet generating devices, by providing a device capable of producing a uniform and high amplitude motion along the nozzle bearing region, as well as providing a separable nozzle plate. This has the advantages of creating droplets with uniform size and velocity, and electronically controllable dispense rate. This in turn enables the precise deposition of liquids, for example for creating thin uniform films of material on a substrate.

SUMMARY OF THE INVENTION

This invention provides a linear droplet generation device, in which the amplitude of the oscillating motion of the nozzle plate is substantially uniform at all the nozzle locations along its length. In a preferred embodiment of the invention, this is achieved by providing a nozzle plate that is curved, e.g. by adding at least one radius of curvature to the nozzle plate, so that it is stiffened in the longitudinal direction. By "longitudinal direction", we mean along/parallel to the long axis of the nozzle plate (which is also along the axis of the linear array of nozzles). In addition to this, the actuator is preferably segmented or slotted, so that longitudinal waves are not strongly excited (i.e. bending of the actuator is preferentially perpendicular to the longitudinal direction), nor are longitudinal waves readily transmitted along the length of the actuator (i.e. there is some degree of mechanical isolation between neighbouring actuator segments).

The curved nozzle plate may be curved across its entire width, or a curved portion may extend over only a part of the width. The radius of curvature may be constant, typically when the curved section extends from one edge to the other edge of the nozzle plate.

The nozzle plate typically has two opposite ends between which the linear array extends. The linear array may extend along a longitudinal axis of the nozzle plate.

The linear array preferably lies entirely within the curved portion.

The curved portion may be a single curve, i.e. a convex or concave shape. Alternatively, there may be a plurality of curved portions and both convex and concave portions may exist on the same nozzle plate.

The curved portion may extend along the longitudinal axis.

The curved portion preferably extends in only one direction, i.e. it is curved out of the plane in which the plate lies. The curve portion is preferably curved only in one dimension.

ASPECTS OF THE INVENTION

A range of aspects of the invention are now disclosed with reference to the following figures.

Figure 1:
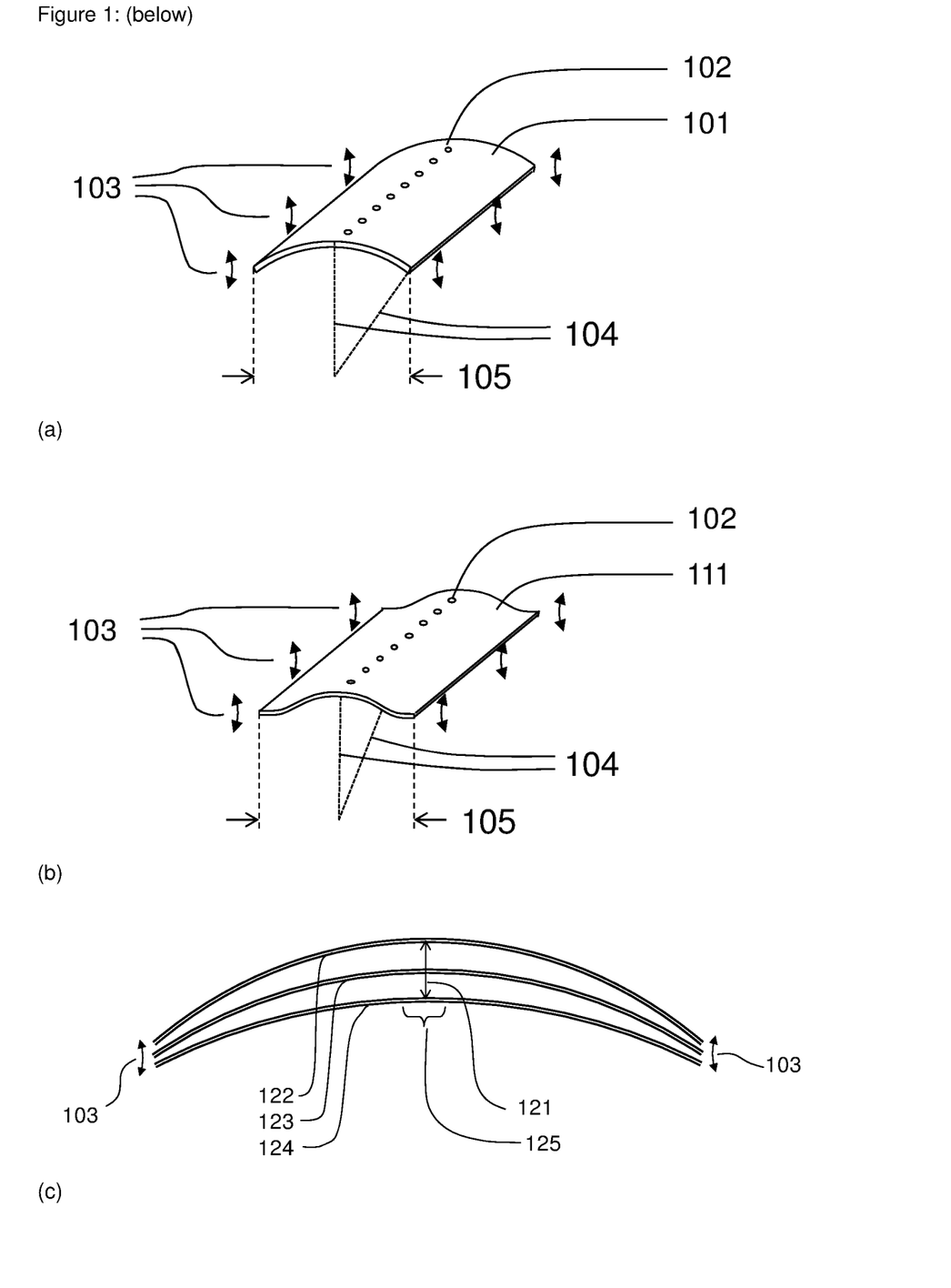
FIGS. 1a to 1c illustrate the curved nozzle plate.

FIG. 1(a) shows a linear nozzle plate (101), in which an array of nozzles (102) is typically formed close to the centre-line of the nozzle plate. This may be a single row of nozzles or a 2-dimensional array or two or more rows of nozzles. The nozzle plate has a characteristic radius of curvature, r (104), and un-supported width, w (105). At one or both edges of the unsupported width, a force and/or torque is applied by the actuator, as illustrated by double-headed arrows (103). A fluid reservoir is located on one side of the nozzle plate and the vibration of the nozzle plate causes an oscillating pressure to be generated in the fluid. This oscillating pressure causes fluid to be ejected through the nozzles. FIG. 1(b) shows a multiply-curved nozzle plate (111), in which the edges remain flat. This can be useful for easier assembly and integration with the actuator. This multiply-curved shape can be achieved using a press tool which deforms to the nozzle plate plastically. In this instance, a flat section can also be provided at the ends of the nozzle plate to allow straightforward sealing of the fluid reservoir. The ends of the nozzle plate may be rigidly clamped or they may be softly supported by a flexible skirt or compliant seal.

In both of the above cases, the nozzle plate is a flexible plate, by which we mean that it is capable of being flexed by the actuating force. However, the magnitude of the vibration (which is typically a few microns) is much less that the magnitude of the static curvature of the nozzle plate (which is typically a few hundred microns). Hence the overall curved shaped of the nozzle plate remains essentially the same while it is being vibrated. FIG. 1(c) shows a schematic end view illustrating the vibration of a curved nozzle plate. At one or both edges of the unsupported width, a force and/or torque is applied by the actuator, as illustrated by the solid arrows (103). The nozzle plate vibrates in response to this, as illustrated by the open arrow (121), providing a high amplitude vibration in the nozzle-bearing region (125). The nozzle plate is shown in its rest position (123), as well as in the extreme upper (122) and lower (124) positions of its vibration. The amplitude of the motion is exaggerated in the illustration, for clarity; in reality the amplitude would typically be less than the thickness of the nozzle plate.

The fluid in the fluid reservoir will have a mass-loading effect on vibration of the nozzle plate. The mass-loading is typically equivalent to a one or two millimetre deep layer of fluid, although this can vary according the boundary conditions in the reservoir. This has the effect of lowering the resonant frequencies of the various vibration modes. The radius of curvature of the nozzle plate is preferably such that the resonant frequency of any longitudinal oscillation modes are above the operating frequency of the device.

Using formulas from "Formulas for Natural Frequency and Mode Shape" by R. D. Blevins, an analytical form of the modal frequency of curved plates is given by:

$$\omega_{ij,curved} = \left[\omega_{ij,flat}^2 + \frac{\alpha_{ij}Eh}{r^2\gamma(1-v^2)}\right]^{\frac{1}{2}}$$

where $$\omega_{ij,flat} = \frac{\lambda_{ij}^2}{L^2}\left[\frac{Eh^3}{12\gamma(1-v^2)}\right]^{\frac{1}{2}}$$

and $\omega_{ij}$ are the angular natural frequencies of the flat and curved plates, $\alpha_{ij}$ and $\lambda_{ij}$ are dimensionless constants for the mode and boundary conditions of interest, E is the elastic modulus of the material, $\gamma$ is the effective mass per unit area (including fluid loading), r is the radius of curvature of the plate, h is the thickness of the plate, L is the length of the plate, v is the Poisson's ratio of the plate material. We can see from these equations that the modes of the curved plate occur at higher frequencies than the corresponding modes in a similar flat plate. The constants $\alpha_{ij}$ and $\lambda_{ij}$ are dependent on the aspect ratio of the plate. For example, for plate length to unsupported width ratio of 2.5, the lowest frequency modes are given by $\lambda_{11}=12.2$, $\lambda_{12}=13.2$, $\alpha_{11}=0.701$ and $\alpha_{12}=0.711$.

As an example, a steel nozzle plate with an unsupported width of w=3.5 mm and thickness of h=0.1 mm is expected to exhibit a first mode around 16 kHz when flat, and 36 kHz when curved with a radius of r=10 mm under certain fluid-loading conditions. Experimentally, the curved plate is found to have good performance at an operating frequency of 23 kHz, whereas the flat plate has a tendency to vibrate non-uniformly at this frequency. This operating regime has the advantage that it is essentially silent, as the operating frequency is ultrasonic. It is especially useful for generating droplets of comparatively large diameter, d, in the range 40 μm<d<400 μm.

As a further example, a steel nozzle plate with an unsupported width of w=2.5 mm and thickness of h=0.15 mm is expected to have a first resonant frequency of around 117 kHz when curved with a radius of 5 mm. An operating frequency of around 100 kHz can then be used to provide uniform motion of the nozzle-bearing region.

The operating frequency of around 100 kHz is found to be especially useful in generating small droplets, with diameters in the range 5 μm<d<50 μm.

As a further example, a steel nozzle plate with an unsupported width of w=6 mm and a thickness of h=0.1 mm is expected to have a first resonant frequency of around 20 kHz when curved with a radius of 20 mm. Drive waveforms with frequency components below 20 kHz can be used with this device to produce uniform ejection of droplets. This would be useful for generating large sized droplets in environments where the acoustic noise associated with operation at audible frequencies can be tolerated.

Figure 2:
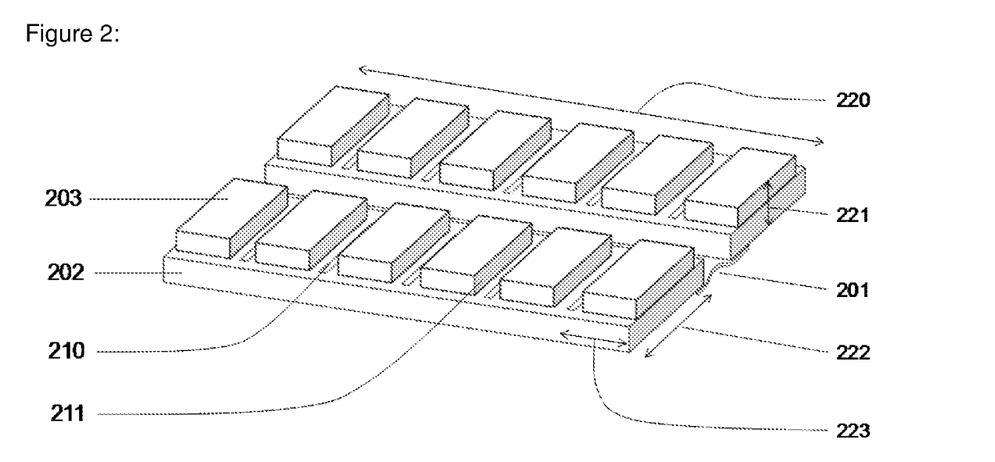
FIG. 2 illustrates an actuator attached to a nozzle plate.

FIG. 2 illustrates a linear actuator attached to a curved nozzle plate (201). In this example, the actuator is a piezoelectric unimorph bending mode actuator, in which strain developed in a piezoelectric layer (203) reacts again a substrate layer (202) to cause a bending motion. It will be apparent to those skilled in the art that this could also be applied to other types of actuator, such as multi-layer piezoelectric bending mode actuators.

The piezoelectric elements (203) and substrate elements (202) are preferably slotted or partially slotted. Piezoelectric materials slots (211) and actuator substrate slots (210) can extend for part or all of the actuator width, W (222) or actuator height, H (221). These slots discourage the propagation of motion in the longitudinal direction (along the length, L, of the actuator (220)), and helps to improve the uniformity of motion at the nozzle locations. The slots or partial slots serve to segment the actuator into "fingers", with width F (223). These fingers are preferably formed with separation comparable to or somewhat less than the actuator width, W (222). The preferred finger width is typically in the range W/3≤F≤W. The segmentation of the actuator into "fingers" means that the forces on the actuator when a voltage is applied are primarily directed into lateral bending motion and not into longitudinal bending motion.

Slots or partial slots may also be included in the nozzle plate, to further isolate regions of the device from neighbouring regions and discourage the propagation of longitudinal bending waves. This can allow a region of the actuator to be energised and generate droplets, whilst a neighbouring region remains comparatively still. A compliant film, such as PET or polyimide can be used to seal any regions of substrate of nozzle plate where the slots penetrate through the thickness.

The actuator may be supported in a flexible manner—for example by bonding to a flexible skirt or resting on a compliant layer such as a closed-cell foam. The soft support can also be used to support and seal the ends of the device, including the ends of the nozzle plate. In the case of soft support, the actuator is designed so that each side enters a resonant bending mode oscillation with half a wavelength across its width, W (222). Alternatively, the actuator can be rigidly supported along its outermost long edges, in which case, it forms a bending mode oscillation with a quarter of a wavelength across its width, W (222). Other support methods may also be applied, such as supporting close to nodal locations of the actuator vibration, where losses due to damping will be lower.

In one embodiment, the operating frequency is approximately 25 kHz, the actuator substrate is 1 mm thick aluminium or 0.7 mm thick steel, and the piezoelectric layer is a 1 mm thick layer of PZT. The actuator width for half-wavelength operation (softly supported) is then around 12 mm and the width for quarter-wavelength operation (anchored) is around 6 mm. More generally, the substrate and piezoelectric layer thickness values can be between 0.1 mm and 3 mm, depending on the operating frequency and power level required for a particular application.

The nozzle plate may be permanently attached to the actuator, or it may be separably attached, so that it can be removed or replaced. The separable nozzle plate arrangement may be used to adjust nozzle sizes or nozzle patterns, to clean or replace blocked or damaged nozzle plates, to avoid cross-contamination between different fluids, or to form part of a consumable fluid package. The nozzle plate may be made separable by mechanical fixings such as screws, cams or levers, by interference fits such as a taper lock or thermal expansion fit, by a removable adhesive or by magnetic attachment.

Figure 3:
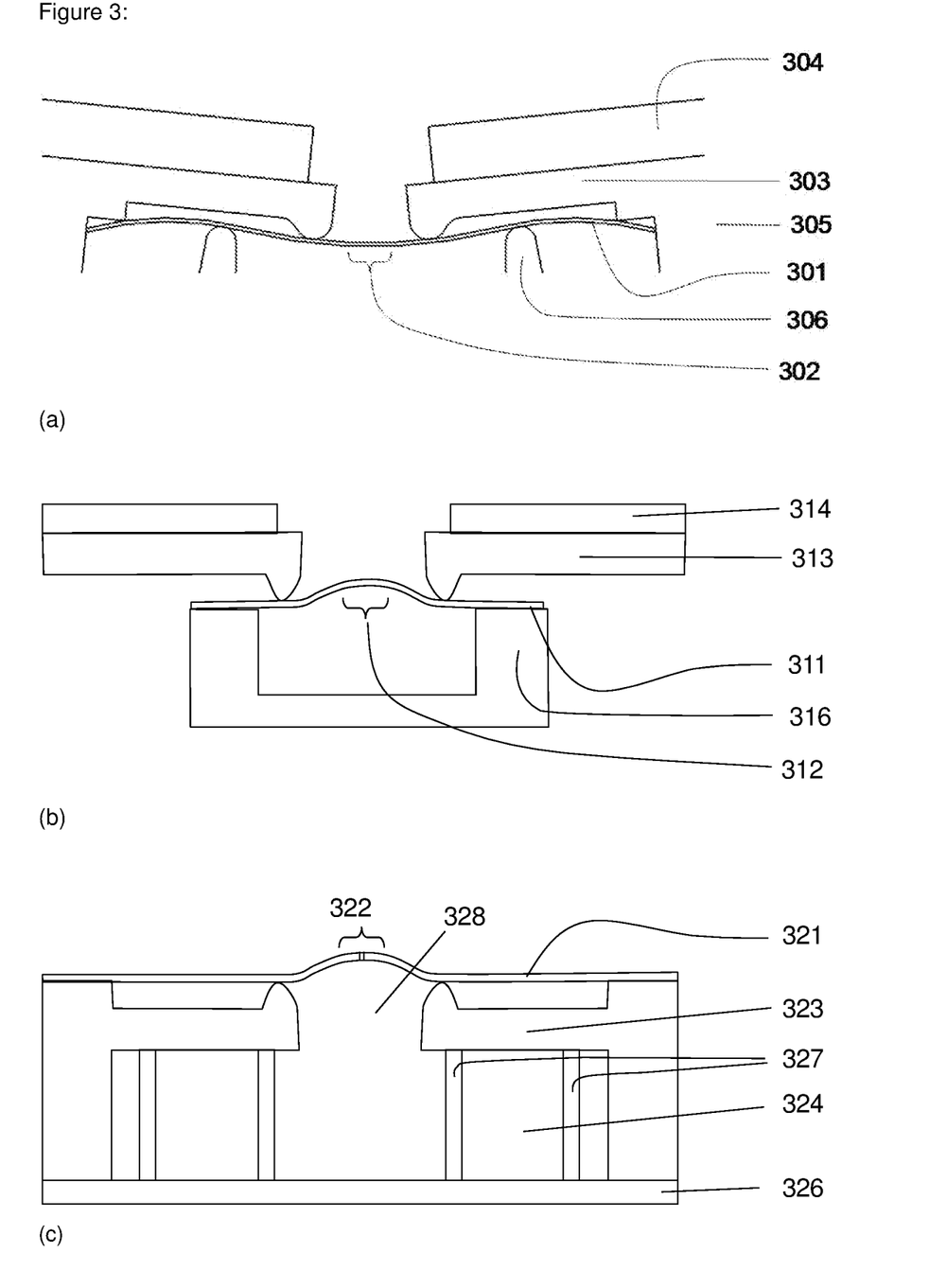
FIGS. 3a to 3c illustrate further droplet generator configurations.

FIG. 3(a) illustrates an arrangement for a separable actuator design. The schematic is shown in cross-section, so that the longitudinal dimension extends out of the page. An actuator, including a piezoelectric layer (304) and substrate layer (303) is removably in contact with a nozzle plate (301) with nozzle-bearing region (302). In this configuration, the actuator presses onto the nozzle plate (301) to provide the force required to vibrate the nozzle plate and cause ejection of droplets. The anchor part of the actuator (305) and the rigid support (306) remain stationary throughout the oscillations. The actuator would typically be segmented in the longitudinal direction as described earlier. The contact points can take the form of contact lines in the longitudinal direction or can be segmented, for example providing one support point per actuator finger. The nozzle plate (301) can be replaced by separating the actuator and support parts from one another, or by sliding the nozzle plate out in the longitudinal direction. An advantage of this arrangement is that the assembly includes some pre-loading, so that the actuator remains in contact with the nozzle plate throughout both positive and negative parts of the sinusoidal oscillation cycle. Another advantage of this arrangement is that the motion of the nozzle-bearing region (302) is amplified compared to the motion of the actuator. Another advantage of this arrangement is that the assembly imposes a curvature on the nozzle plate, removing the need for a separate doming process to produce a curved nozzle plate.

FIG. 3(b) illustrates an alternative arrangement for a separable actuator design. In this configuration, the nozzle plate (311) with nozzle-bearing region (312) is permanently fixed to a rigid support (316). The actuator (comprising actuator substrate (313) and piezoelectric elements (314)) presses on the nozzle plate and imparts a vibration to it. This has the advantages of providing a more robust consumable element, which can also be supplied charged with fluid for ejection. In comparison to FIG. 3(a), this arrangement also has the advantage of a smaller number of contact points/lines between moving parts, which are better controlled.

Figure 4:
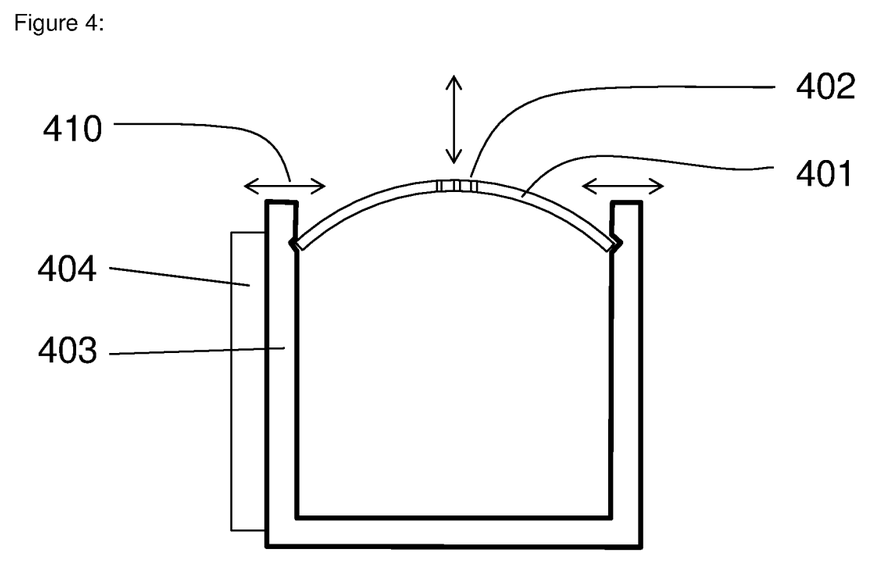
FIG. 4 illustrates an alternative droplet generator configuration.

FIG. 3(c) illustrates an alternative arrangement for an actuator design. In this design, the piezoelectric element (324) is located on the inside of the fluid chamber (328). The actuator can operate in axial expansion/contraction mode or in thickness-shear mode, so that the actuator arm (323) is deflected, which in turn moves the nozzle plate (321). A protective layer (327) may be used to protect the piezoelectric element (324) from the fluid. This approach has the advantages that a comparatively large volume of piezoelectric material can be used within a compact actuator design and that the piezoelectric material is located inside the actuator. Having the piezoelectric material inside the actuator helps to protect it from damage and to protect the user from voltages applied to the actuator. It also provides best access to the spray plume, for example, so that a highly divergent spray can be used, a target for droplet deposition can be placed in close proximity to the droplet generator, and the user can easily observe the spray plume as it emerges from the nozzle-bearing region (322).

The droplet generators in FIGS. 2 and 3(*a*)-(*c*) are illustrated as "double sided"—i.e. with an actuator on each side of the nozzle plate. However, in any of these configurations, the actuator can alternatively be a "single-sided" design, in which a rigid wall is used in place of one of the actuators. This approach has the advantages of compactness and reduced part count, but has the disadvantage that the maximum power that can be applied is approximately halved.

FIG. 4 illustrates an alternative arrangement for an actuator. In this arrangement, the nozzle plate (401) is squeezed laterally by the actuator and vibrates up and down, as shown by the double-headed arrows (410). The actuator is shown as a piezoelectric unimorph with piezoelectric layer (404) and substrate layer (403), although bi-morph or multi-layer actuators could be used instead. A mechanical pre-load is typically applied so the parts remain in contact throughout the oscillation cycle. An advantage of this arrangement is that a mechanical advantage is gained due to the curved nozzle plate, so that the nozzle-bearing region (402) vibrates with a greater amplitude than the actuator (403). Another advantage of this arrangement is that the nozzle plate can be replaced either by opening up the jaws of the actuator or by further bending the nozzle plate. Another advantage of this actuator is that the nozzle plate does not have to be pre-shaped using a doming tool, as the curvature can be imparted by the pre-load from the actuator. The actuator would typically be segmented in the longitudinal direction as described earlier.

Figure 5:
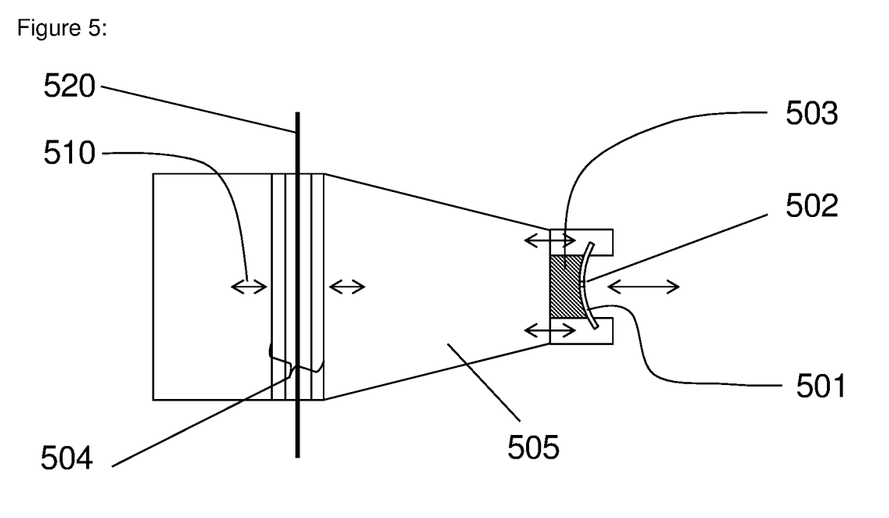
FIG. 5 illustrates an alternative droplet generator configuration.

FIG. 5 illustrates an alternative arrangement for an actuator. In this embodiment of the invention, the curved nozzle plate is coupled to an axial-mode actuator. The axial mode actuator can be one or more cylindrical actuators. These are typically constructed from a metal actuator body (505) including a central bolt and PZT rings (504), held by a mechanical support ring (520). The vibration is illustrated with double-headed arrows (510). Alternatively, the axial-mode actuator can comprise of one or more monolithic multi-layer piezoelectric actuator chips, such as those available from Noliac and PI Ceramic. Other axial-mode actuators could also be used. In this design, the nozzle plate (501) is held at the edges and the actuator vibrates the nozzle plate, potentially with the motion of the nozzle-bearing region (502) being further amplified. The fluid reservoir may also be vibrated in this configuration, which can provide an additional source of pressure oscillations in the fluid (503). However, one or more compliant walls of the reservoir can be used to ensure that pressure oscillations are generated primarily in response to the vibration of the nozzle plate.

An example of such an actuator, operating at around 25 kHz, has an outer diameter of 40 mm and a total length of 88 mm. The front face diameter of 23 mm allows a nozzle plate of 15 mm length to be clamped in place with a pre-defined curvature.

Figure 6:
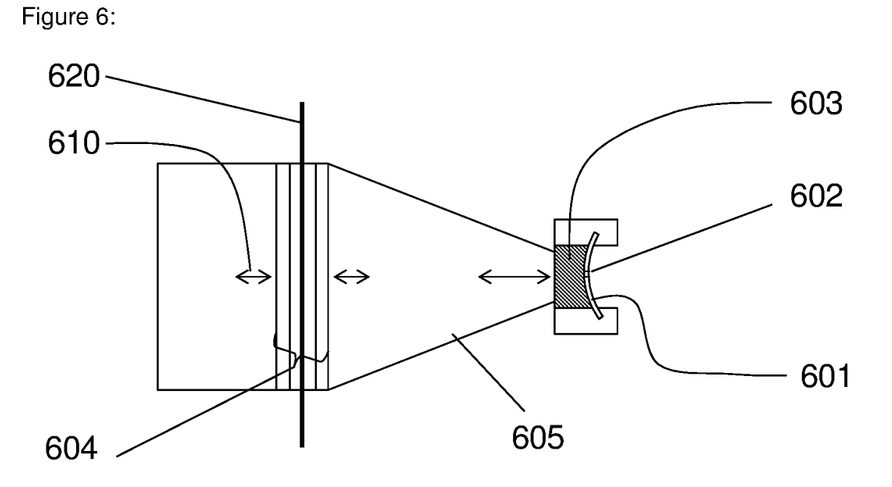
FIG. 6 illustrates an alternative droplet generator configuration.

FIG. 6 illustrates an arrangement where the back wall of the fluid-filled chamber (603) is vibrated. The vibration is illustrated with double-headed arrows (610). The illustration shows this motion being excited by an axial-mode actuator (605). Pressure oscillations induced in the fluid are then transmitted to the front of the fluid chamber, so that fluid is ejected from the nozzles (602). The nozzle plate (601) may also vibrate in response to these pressure oscillations. In this arrangement, the curved nozzle plate is still beneficial to provide control of longitudinal vibration modes and uniform ejection along the length of the nozzle plate.

Many of the embodiments shown here use bending-mode piezoelectric unimorph actuators. In general, bimorph or multi-layer actuators can be substituted where greater force or displacement per volt is required. Axial mode actuators can be substituted where greater force or robustness is required. Electrostrictive or magnetostrictive actuators can also be applied in a similar manner to achieve the same objective.

The actuator substrate material is preferably stainless steel or aluminium. The nozzle plate material is preferably stainless steel, nickel or polyimide. In the case that a polymer (such as polyimide) is used for the nozzles, the polyimide may be supported by a stiffer layer (such as stainless steel) close to the nozzles, forming a steel-polyimide composite nozzle plate.

Figure 7:
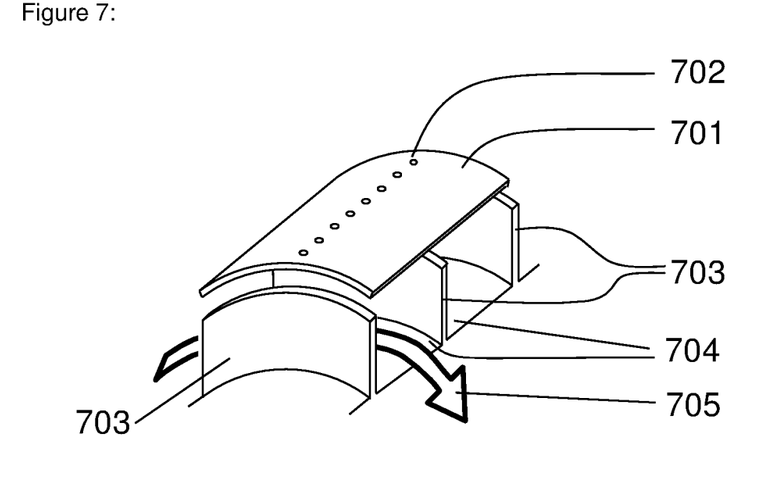
FIG. 7 illustrates a droplet generator with baffles in the fluid feed.

FIG. 7 illustrates a fluid feed arrangement in combination with the actuator. The fluid feed has one or more baffles (703), which extend perpendicular to the nozzle plate. The baffles, back wall and nozzle plate (701) define two or more channels (704), through which fluid can be circulated as illustrated in one of the channels by the arrow (705). The baffles preferably extend close to the nozzle plate, but do not touch it, a gap of less than 0.5 mm being preferred. In addition to this, a compliant seal between the baffles (703) and the nozzle plate (701) is desirable, but this is not practical for all applications. The baffles are preferably thin (less than 1 mm thickness) and rigid. They preferably are spaced approximately every 5 mm, although one baffle per nozzle can be used, or they can be as far as 50 mm apart and still provide some benefits. The baffles serve several purposes, as described below. The main purpose of the baffles is to reduce the longitudinal propagation of pressure waves in the fluid. Without the baffles present, regions of the head can suffer from "fluidic cross-talk" whereby high amplitude pressure oscillations in one region can reduce the amplitude of pressure oscillations in a neighbouring region. A series of thin, rigid baffles can greatly reduce this fluidic cross-talk, without otherwise impairing the operation of the device. Another purpose of the baffles is to control the delivery of fluid to the nozzles (702). In the case of a circulating fluid feed, in which only a fraction of the fluid circulating in the device is ejected, they ensure that fluid is supplied uniformly to the whole of the nozzle-bearing region. A third purpose of the baffles is to control the average pressure (bias pressure) at which fluid is presented to the nozzle plate (701), such that the bias pressure is substantially uniform throughout the nozzle-bearing region. A uniform cross-flow velocity, shear rate and bias pressure in the fluid are beneficial to produce uniform ejection of droplets.

The invention claimed is:

1. A liquid droplet production apparatus comprising:
a curved nozzle plate, comprising: a flexible substrate having a linear array of nozzles that extend through said nozzle plate,
said nozzles being arranged in at least one line along a longitudinal axis of the nozzle plate, forming thereby a nozzle-bearing region,
wherein the nozzle plate has a curvature so as to impart an increased longitudinal stiffness to it;
a fluid reservoir for supplying liquid to at least the nozzle bearing region of one face of the nozzle plate; and
an actuator for vibrating the nozzle plate to cause liquid droplets to be ejected from the other side of the nozzle plate,
wherein the actuator comprises an upper layer and a lower layer, said lower layer of the actuator comprising a plurality of slots or partial slots along its length, wherein the plurality of slots or partial slots comprises a first set of slots on a first side of the lower layer and a second set of slots on a second side of the lower layer, said slots or partial slots being perpendicular to the longitudinal axis of the nozzle plate.

2. A nozzle plate according to claim 1, wherein the substrate is curved over only a portion of its entire width.

3. A nozzle plate according to claim 2, wherein the substrate is curved in only one dimension.

4. A liquid droplet production apparatus according to claim 2, wherein the nozzle plate thickness, t, is in the range 0.01 mm<t<1 mm.

5. A liquid droplet production apparatus according to claim 2, wherein the actuator is a piezoelectric actuator, and further wherein the actuator is a bending mode actuator or an axial-mode actuator.

6. A nozzle plate according to claim 1, wherein the substrate is curved in only one dimension.

7. A liquid droplet production apparatus according to claim 6, wherein the nozzle plate thickness, t, is in the range 0.01 mm<t<1 mm.

8. A liquid droplet production apparatus according to claim 6, wherein the actuator is a piezoelectric actuator, and further wherein the actuator is a bending mode actuator or an axial-mode actuator.

9. A liquid droplet production apparatus according to claim 1, wherein a nozzle plate thickness, t, is in the range 0.01 mm<t<1 mm.

10. A liquid droplet production apparatus according to claim 9, wherein the nozzle plate thickness, t, is about 0.1 mm.

11. A liquid droplet production apparatus according to claim 9, wherein a curved portion of the nozzle plate has a constant radius of curvature, and a nozzle plate radius of curvature, r, is in the range 2 mm<r<50 mm.

12. A liquid droplet production apparatus according to claim 11, wherein a curved portion of the nozzle plate is unsupported across its width, w, where w is in the range 1 mm<w<8 mm and where a nozzle plate length, L, is greater than the unsupported width, w, such that L>4 w.

13. A liquid droplet production apparatus according to claim 12, wherein the nozzle plate width, w, is about 3 mm.

14. A liquid droplet production apparatus according to claim 11, wherein the nozzle plate radius of curvature, r, is about 10 mm.

15. A liquid droplet production apparatus according to claim 1, wherein the actuator has an operation frequency, f, that is in the range 1 kHz<f<150 kHz.

16. A liquid droplet production apparatus according to claim 15, wherein the operation frequency, f, is about 25 kHz.

17. A liquid droplet production apparatus according to claim 1, wherein the actuator is a piezoelectric actuator, and further wherein the actuator is a bending mode actuator or an axial-mode actuator.

18. A liquid droplet production apparatus according to claim 17, wherein the actuator is a piezoelectric unimorph, wherein the lower layer comprises a metal layer and the upper layer comprises a piezoelectric layer, and wherein the metal layer and piezoelectric layers each have a thickness in the range 0.1 mm to 3 mm.

19. A liquid droplet production apparatus according to claim 18, wherein the metal layer is about 1 mm thick aluminium or 0.7 mm thick steel and the piezoelectric layer is about 1 mm thick PZT.

20. A liquid droplet production apparatus according to claim 19, wherein the actuator has an operation frequency, and an actuator width, W, is about half of a bending wavelength at the operation frequency.

21. A liquid droplet production apparatus according to claim 19, wherein the actuator has an operation frequency, and an actuator width, W, is about a quarter of a bending wavelength at the operation frequency and is anchored at its outer edge.

22. A liquid droplet production apparatus according to claim 1, wherein the plurality of slots or partial slots in the actuator are spaced so as to form fingers with a width, F, where F is in the range $W/3 \leq F \leq W$.

23. A liquid droplet production apparatus according to claim 1, wherein the actuator moves a series of actuator fingers, which in turn impart motion to the nozzle plate.

24. A liquid droplet production apparatus according to claim 1, wherein the actuator squeezes the nozzle plate from the sides, pushing the longitudinal edges of the nozzle plate substantially towards one another.

25. A liquid droplet production apparatus according to claim 24, wherein the actuator is a piezoelectric actuator, with a diameter of about 40 mm, operating at about 25 kHz.

* * * * *